(12) United States Patent
Zhang et al.

(10) Patent No.: US 11,377,465 B2
(45) Date of Patent: Jul. 5, 2022

(54) PYRANOGLUCOSE-SUBSTITUTED PYRAZOLE COMPOUND, PREPARATION METHOD THEREOF AND APPLICATION THEREOF

(71) Applicants: Yabao Pharmaceutical Group Co., Ltd., Shanxi (CN); Suzhou Yabao Pharmaceutical R&D Co., Ltd., Jiangsu (CN)

(72) Inventors: Fei Zhang, Jiangsu (CN); Peng Wang, Jiangsu (CN); Lili Sun, Jiangsu (CN); Lin Zhu, Jiangsu (CN)

(73) Assignees: Yabao Pharmaceutical Group Co., Ltd., Shanxi (CN); Suzhou Yabao Pharmaceutical R&D Co., Ltd., Jiangsu (CN)

( * ) Notice: Subject to any disclaimer, the term of this patent is extended or adjusted under 35 U.S.C. 154(b) by 108 days.

(21) Appl. No.: 16/960,858

(22) PCT Filed: Jan. 17, 2019

(86) PCT No.: PCT/CN2019/072148
§ 371 (c)(1),
(2) Date: Jul. 8, 2020

(87) PCT Pub. No.: WO2019/141209
PCT Pub. Date: Jul. 25, 2019

(65) Prior Publication Data
US 2021/0061840 A1  Mar. 4, 2021

(30) Foreign Application Priority Data
Jan. 18, 2018 (CN) .......................... 201810052483.8

(51) Int. Cl.
*A61P 3/10* (2006.01)
*C07H 17/02* (2006.01)

(52) U.S. Cl.
CPC .................... *C07H 17/02* (2013.01)

(58) Field of Classification Search
CPC ....................................................... A61P 3/10
See application file for complete search history.

(56) References Cited

FOREIGN PATENT DOCUMENTS

| CN | 1688597 A | 10/2005 |
|---|---|---|
| CN | 1950389 A | 4/2007 |
| CN | 102675378 A | 9/2012 |
| CN | 103596944 A | 2/2014 |

(Continued)

OTHER PUBLICATIONS

SK, "Acyl Protective Groups", Chem-Station Int. Ed, Apr. 3, 2014, 6 pgs; retrieved from https://en.chem-station.com/author/sk.

(Continued)

*Primary Examiner* — John S Kenyon
(74) *Attorney, Agent, or Firm* — Umberg Zipser LLP; Jason Tejani

(57) ABSTRACT

A pyranoglucose-substituted pyrazole compound, used as a pharmaceutical intermediate, having the structural formula represented by formula (9c). The present invention further relates to an intermediate compound represented by formula (10c) or a salt thereof. The present invention further relates to a preparation method of the aforementioned intermediate compound and a method of using the same to prepare an SGLT inhibitor. By means of the novel key intermediate, the preparation technique of an SGLT inhibitor is greatly simplified. In addition, because the intermediate can be precipitated in the form of a salt and is easy to purify, the purity of the SGLT inhibitor is significantly increased, compared with the original preparation pathway (crude product purity can reach 99% or more). (I)

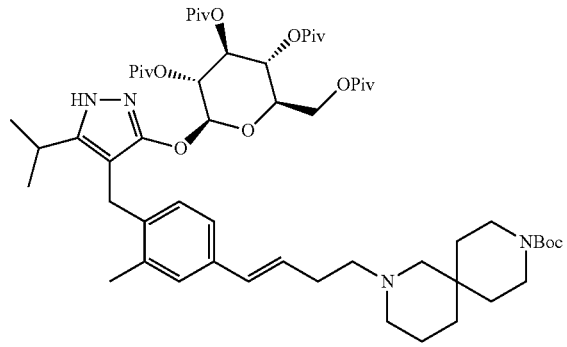

(9c)

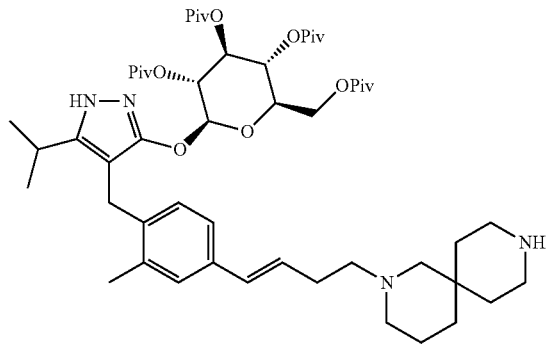

(10c)

18 Claims, 3 Drawing Sheets

(56) References Cited

FOREIGN PATENT DOCUMENTS

| | | | |
|---|---|---|---|
| CN | 104284894 A | 1/2015 | |
| CN | 105008379 A | 10/2015 | |
| CN | 105705509 A | 6/2016 | |
| WO | 2007129668 A1 | 11/2007 | |
| WO | 2013169546 A1 | 11/2013 | |
| WO | WO-2013169546 A1 * | 11/2013 | ........... A61K 31/706 |
| WO | 2014055297 A1 | 4/2014 | |
| WO | 2015069541 A1 | 5/2015 | |

OTHER PUBLICATIONS

Office Action for CN201810052483.8 dated Mar. 29, 2021; 4 pgs.

* cited by examiner

PYRANOGLUCOSE-SUBSTITUTED PYRAZOLE COMPOUND, PREPARATION METHOD THEREOF AND APPLICATION THEREOF

This application claims the priority of the Chinese Patent Application No. 201810052483.8, with the title of "Pyranoglucose-substituted pyrazole compound and preparation method thereof", filed on Jan. 18, 2018 before the China National Intellectual Property Administration, which is hereby incorporated by reference in its entirety.

FIELD OF THE INVENTION

The present application belongs to the field of medicinal chemistry, and relates to a pyranoglucose-substituted pyrazole compound used as a pharmaceutical intermediate, and preparation method and application thereof.

BACKGROUND OF THE INVENTION

Diabetes is a group of lifelong metabolic diseases characterized by chronic hyperglycemia and caused by multiple causes. Long-term hyperglycemia will cause damages to large vessels and capillary vessels and will endanger the heart, brain, kidneys, peripheral nerves, eyes, feet, etc. According to the statistics of the World Health Organization, there are more than 100 complications of diabetes, which is currently known as a disease with the most complications, and the incidence rate thereof is increasing. The kidney plays a very important role in glycometabolism of the body. Glucose cannot pass through the lipid bilayer of the cell membrane freely in the body, and must rely on the glucose transporter on the cell membrane. Sodium-coupled glucose cotransporters (SGLTs) are one of the transporters known to be responsible for the absorption of carbohydrates such as glucose. More specifically, SGLT1 is responsible for transporting glucose across the brush border membrane of the small intestine. Inhibition of SGLT1 can lead to a reduction in glucose absorption in the small intestine, and thus it can be used for the treatment of diabetes.

Eli Lilly and Company has studied and developed a new inhibitor of SGLTs for alternative medicines and treatments of diabetes. CN105705509 discloses a SGLTs inhibitor—pyrazole compound with the structure of formula (1):

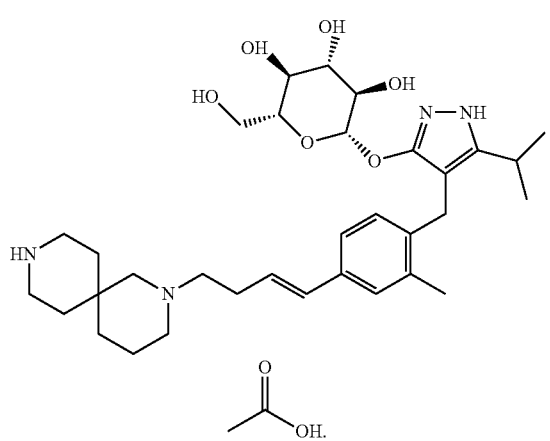

1

As we all know, there are strict requirements for the production process of drugs. The purity of the active ingredients of drugs will directly affect the quality, safety and effectiveness of drugs. It is very important to optimize and simplify the synthetic route and to strictly control the purity of the intermediates for improving drug production, optimizing quality control and formulation development.

CN105705509 discloses a method for synthesizing the compound of formula (1), wherein the intermediate compound of tert-butyl 2-{(3E)-4-[3-methyl 4-({5-(propan-2-yl)-3-[(2,3,4,6-tetra-acetyl-β-D-glucopyranosyl) oxy]-1H-pyrazol-4-yl} methyl) phenyl] but-3-en-1-yl}-2,9-diazaspiro [5.5] undecane-9-formate (compound obtained in Preparation Example 12b) is obtained by step B of Scheme 4, which is a yellow foam with a yield of 68.6% and a purity of 94%. This step involves purification with silica gel column, and has low production efficiency, high cost and poor quality controllability. The intermediate 2-{(3E)-4-[3-methyl 4-({5-(propan-2-yl)-3-((2,3,4,6-tetra-acetyl-β-D-glucopyranosyl) oxy)-1H-pyrazol-4-yl} methyl) phenyl] but-3-en-1-yl}-2,9-diazaspiro [5.5] undecane (the compound obtained in Preparation Example 18) is obtained by step C of Scheme 4, which is a yellow solid with a purity of 95.0%. Both of the intermediate compounds in the above two steps are obtained with relatively low purity. Moreover, the purity of the compound of formula (1) prepared by the method in paragraphs 0141 and 0142 in the publication of CN105705509 is 96.7%. The purity of the final compound obtained is not adequate, which is not conducive to the subsequent drug preparation process.

Therefore, in view of the defects of the above process, it is urgent to develop new intermediates and route for synthesizing the compound of formula (1), to simplify the production process and improve the controllability of product quality.

SUMMARY OF THE INVENTION

The technical problem to be solved by the present application is to overcome the shortcomings of the prior art and provide a new key intermediate for synthesizing the compound of formula (1), including the compound of formula (9c) and the compound of (10c) or the salt thereof. Further, the present application also provides a method of preparing the above intermediate and a new synthetic route of the compound of formula (1). According to the preparation method of the present application, the compound of formula (9c) can be precipitated in the form of crystals; and the compound of formula (10c) or the salt thereof can be precipitated in the form of crystals, resulting in a crude intermediate product with high purity. Therefore, the synthetic process of the compound of formula (1) is simplified remarkably with reduced cost and increased yield, and is suitable for industrial production. The key intermediates and synthetic routes of the present application can be used to produce the compound of formula (1) with high purity.

One of the objects of this application is to provide a key intermediate for synthesizing the compound of formula (1) as a SGLTs inhibitor.

Another object of the present application is to provide a method of preparing the key intermediate.

Another object of the present application is to provide use of the key intermediate in the preparation of the compound of formula (1).

Another object of the present application is to provide a method for preparing the compound of formula (1).

The first aspect of the present application relates to a compound of formula (9c),

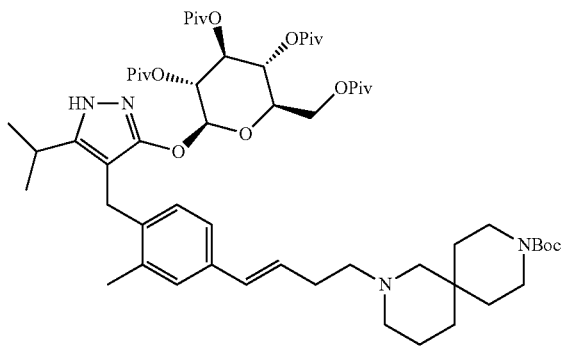

9c wherein Piv is pivaloyl.

Another aspect of the present application relates to a method for preparing the compound of formula (9c), comprising reacting a compound of formula (16) or a salt thereof with a compound of formula (17) to obtain a compound of formula (9c):

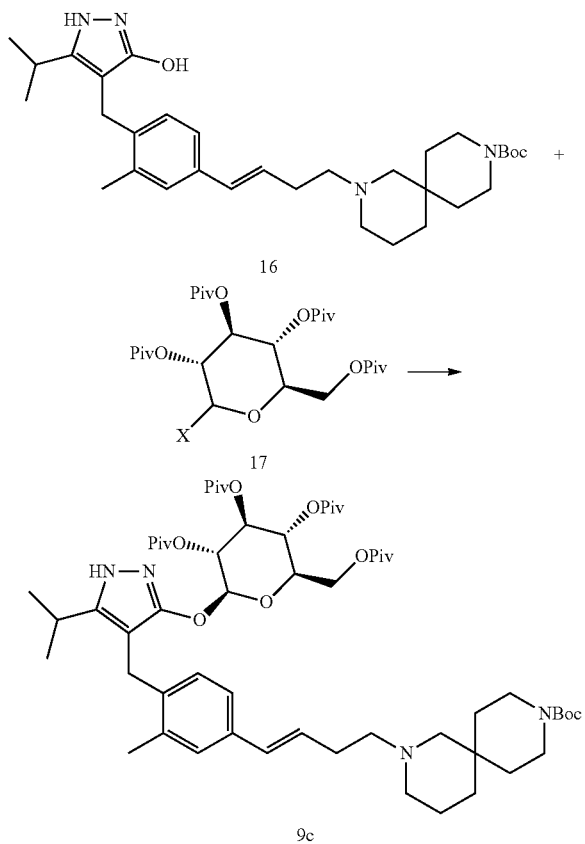

wherein, X is a leaving group and Piv is pivaloyl.

In some embodiments of the method for preparing the compound of formula (9c), the leaving group X may be selected from the group consisting of halogen, methanesulfonate, triflate or p-toluenesulfonate, preferably halogen.

As used herein, the "halogen" refers to fluorine, chlorine, bromine and iodine, etc.

As used herein, the "Boc" refers to tert-butoxycarbonyl.

In some embodiments of the method for preparing the compound of formula (9c), the salt of the compound of formula (16) may be hydrochloride, acetate, maleate or succinate, etc In some embodiments of the method for preparing the compound of formula (9c), the reaction is performed in a first reaction solvent under a basic condition.

In one embodiment of the method for preparing the compound of formula (9c) of the present application, the compound of formula (9c) as an intermediate is prepared as follows:

(1) reacting the compound of formula (16) with the compound of formula (17) in the first reaction solvent under a basic condition for 4-5 hrs at a temperature of 40-45° C.;

(2) after the reaction is completed, cooling, filtering, dissolving the filtered solid into a first organic solvent and water to remove an inorganic salt, adding a first poor solvent to precipitate a solid, filtering and then vacuum drying to obtain the compound of formula (9c).

In some embodiments, the first organic solvent can be ethyl acetate.

In some embodiments, the first poor solvent can be one selected from the group consisting of acetonitrile, methyl tert-butyl ether, diethyl ether, n-heptane, n-hexane, and cyclohexane, or any combination thereof.

In some embodiments of the above method for preparing the compound of formula (9c), the base used in the basic condition can be carbonate, phosphate, bicarbonate, hydrogen phosphate, and/or the like. In an embodiment, the counter cation for carbonate, phosphate, bicarbonate and biphosphate can be an alkali metal.

According to the present application, the first reaction solvent is not particularly limited, preferably, is a solvent that can dissolve the compounds of formula (16) and formula (17).

As an example, the first reaction solvent can be one, two or more of polar solvents.

For example, in some embodiments of the above method for preparing the compound of formula (9c), the first reaction solvent can be one selected from the group consisting of acetonitrile, N,N-dimethylformamide, tetrahydrofuran, and ethyl acetate, or any combination thereof.

Another aspect of the present application relates to an intermediate compound of formula (10c), or a salt thereof,

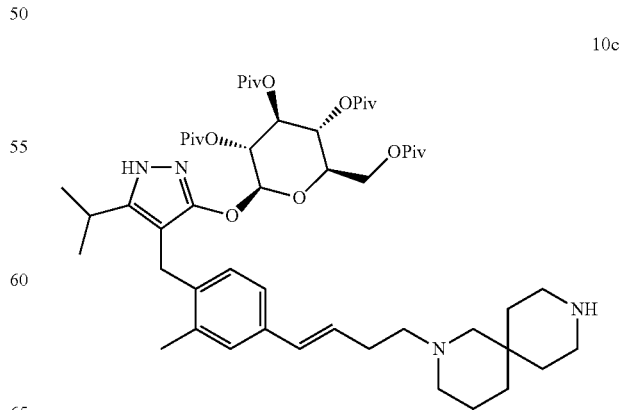

10c wherein Piv is pivaloyl.

Preferably, the salt of the compound of formula (10c) is methanesulfonate or p-toluenesulfonate.

Another aspect of this application relates to a method for preparing a compound of formula (10c) or a salt thereof, comprising reacting a compound of formula (9c) with an acid to obtain the compound of formula (10c) or a salt thereof;

In some embodiments, the second poor solvent is one selected from the group consisting of n-heptane, n-hexane, cyclohexane, and methylcyclohexane, or any combination thereof.

In some embodiments, the base used to neutralize the excessive acid is potassium hydroxide; and the second poor solvent is n-heptane.

In an embodiment of step (a), the acid may be added to the second reaction solvent in batches.

Another aspect of the present application relates to use of the compound of formula (9c), or the intermediate compound of formula (10c), or the salt thereof for preparing the compound of formula (1);

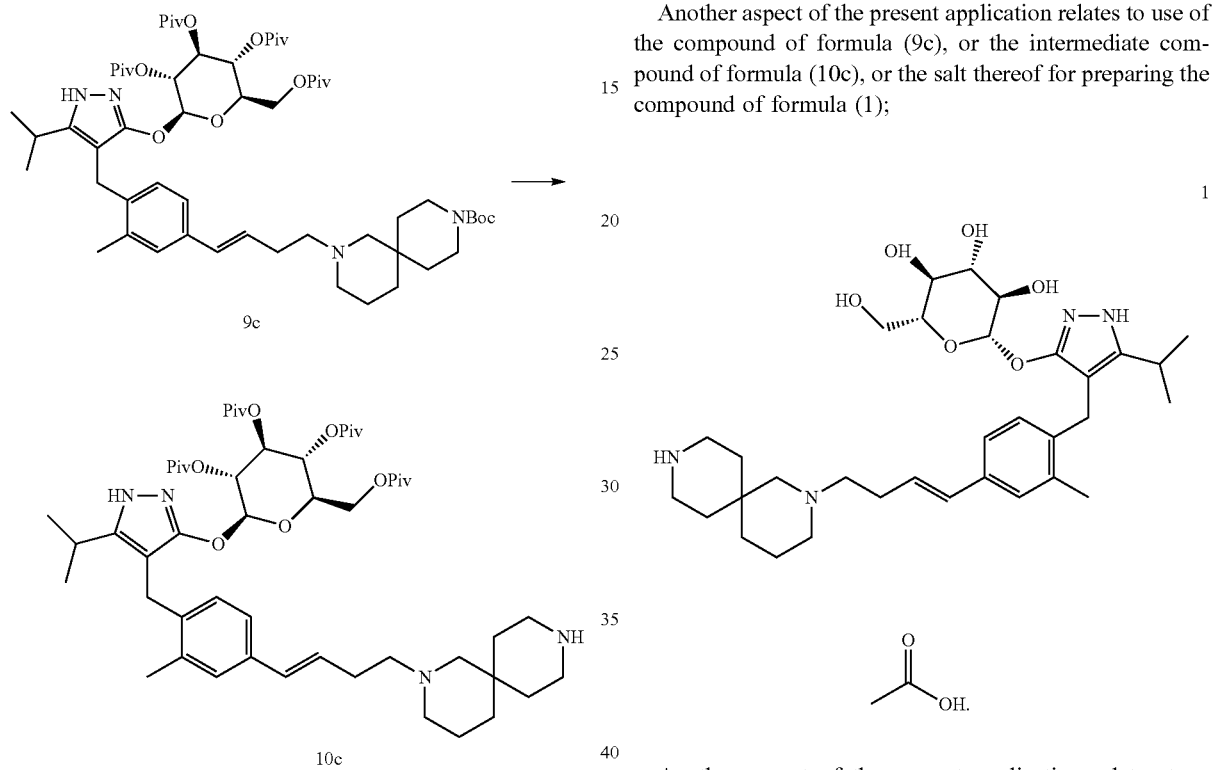

wherein Piv is pivaloyl.

In one embodiment, the method for preparing an intermediate compound of formula (10c) or a salt thereof of the present application comprising:
(a) reacting the compound of formula (9c) with the acid in a second reaction solvent for 2-3 hrs at a temperature of 15-20° C.; wherein the second reaction solvent is one selected from the group consisting of ethyl acetate, butyl acetate, methyl acetate, isopropyl acetate, methylene chloride and chloroform, or any combination thereof; the acid is one of methanesulfonic acid, p-toluenesulfonic acid and p-toluenesulfonic acid monohydrate, or any combination thereof;
(b) after the reaction is completed, neutralizing an excessive acid with a base, adding a second poor solvent to precipitate a solid, filtering and then vacuum drying to obtain the compound of formula (10c) or a salt thereof.

In some embodiments, the base used to neutralize the excessive acid is one selected from the group consisting of potassium hydroxide, sodium carbonate, sodium bicarbonate, potassium carbonate, potassium bicarbonate, sodium phosphate, disodium hydrogen phosphate, potassium phosphate, and sodium hydroxide, or any combination thereof.

Another aspect of the present application relates to a method for preparing a compound of formula (1), comprising:

(I) subjecting the compound of formula (10c) or the salt thereof to hydrolysis or alcoholysis under a basic condition to obtain the compound of formula (11); and

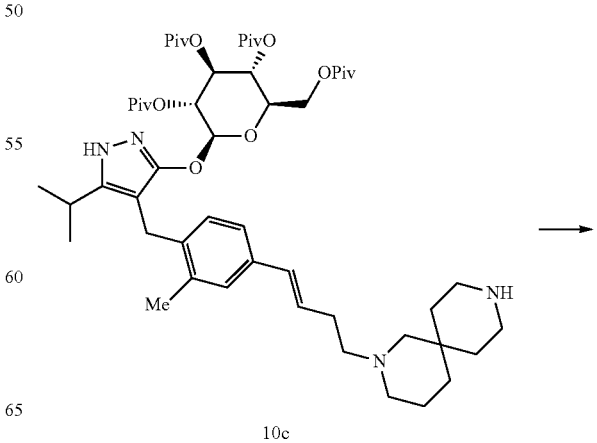

-continued

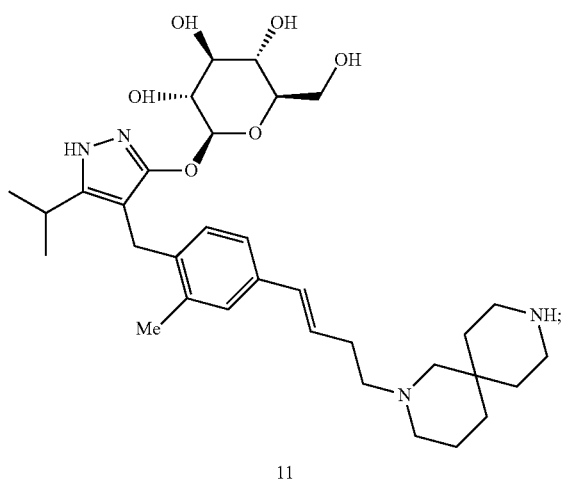

11

(II) reacting the compound of formula (11) with acetic acid to obtain the compound of formula (1);

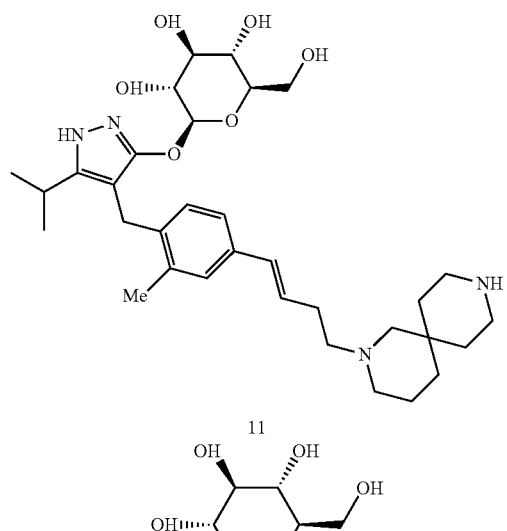

11

AcOH

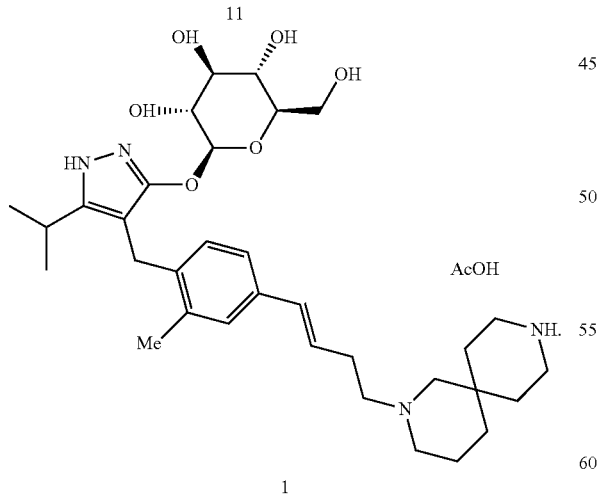

1

In some embodiments of the method for preparing the compound of formula (1) of the present application, the compound of formula (10c) or a salt thereof can be obtained by:

(III) reacting a compound of formula (16) or a salt thereof with a compound of formula (17) to obtain the compound of formula (9c), wherein X is a leaving group and Piv is pivaloyl;

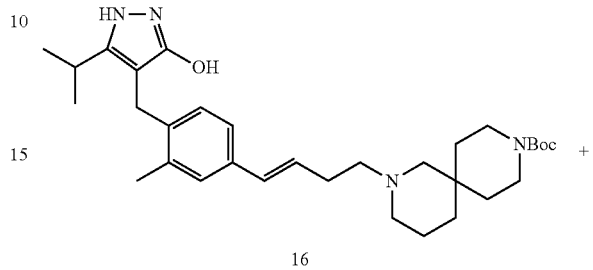

16

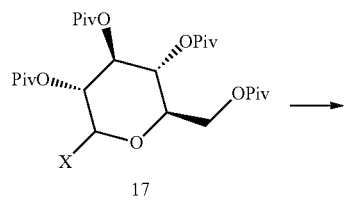

17

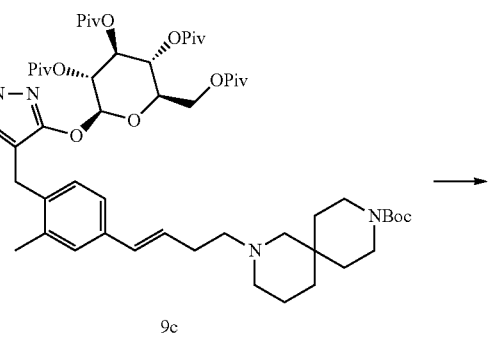

9c and (IV) reacting the compound of formula (9c) with an acid to obtain the compound of formula (10c) or the salt thereof;

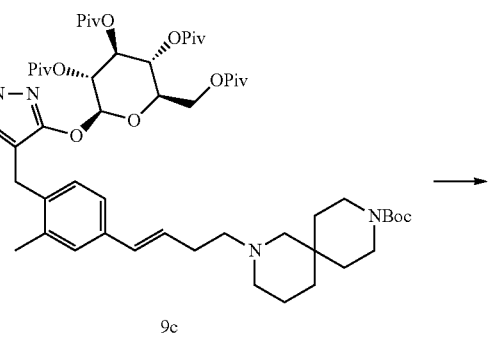

9c

-continued

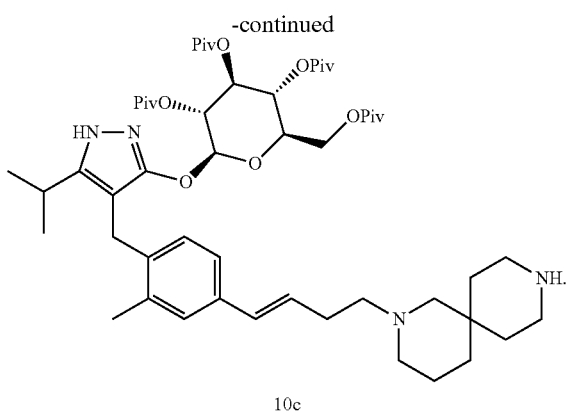

10c

In some embodiments of the method for preparing the compound of formula (1) of the present application, step (I) is performed by:
subjecting the compound of formula (10c) or a salt thereof to hydrolysis or alcoholysis under a basic condition at a temperature of 45-50° C., and cooling and filtering after the reaction is completed to obtain a filtrate containing the compound of formula (11); wherein the hydrolysis is performed with one or both of water-containing ethanol and methanol; the alcoholysis is performed with one or both of anhydrous ethanol and methanol; the base used in the basic condition is one selected from the group consisting of potassium hydroxide, sodium hydroxide, DBU (1,8-diazabicyclo [5,4,0]-undec-7-ene), sodium methoxide and sodium ethoxide, or any combination thereof; and
step (II) is performed by:
adding acetic acid into the obtained filtrate containing the compound of formula (11) and stirring, then adding ethyl acetate and water dropwise, stirring for another 3-4 hrs, and after the reaction is completed, filtering, rinsing, and vacuum drying to obtain the compound of formula (1).

In some embodiments of the method for preparing the compound of formula (1) of the present application,
step (III) is performed by:
reacting the compound of formula (16) or the salt thereof with the compound of formula (17) under a basic condition in the first reaction solvent at temperature of 40-45° C. for 4-5 hrs to obtain the compound of formula (9c), wherein the leaving group X of the compound of formula (17) is selected from the group consisting of halogen, methanesulfonate, triflate or p-toluenesulfonate; the salt of the compound of formula (16) is selected from the group consisting of hydrochloride, acetate, maleate and succinate; the base used in the basic condition is one selected from the group consisting of carbonate, phosphate, bicarbonate and hydrogen phosphate, or any combination thereof; the first reaction solvent is one selected from the group consisting of acetonitrile, N,N-dimethylformamide, tetrahydrofuran, and ethyl acetate, or any combination thereof; after the reaction is completed, cooling, filtering, dissolving the filtered solid in a first organic solvent and water to remove an inorganic salt, adding the first poor solvent to precipitate a solid, and filtering and then vacuum drying to obtain the compound of formula (9c); preferably, the first organic solvent is ethyl acetate; further preferably, the first poor solvent is one selected from the group consisting of acetonitrile, methyl tert-butyl ether, diethyl ether, n-heptane, n-hexane, and cyclohexane, or any combination thereof; and step (IV) comprises:
(a1) reacting the compound of formula (9c) with an acid in a second reaction solvent at a temperature of 15-20° C. for 2-3 hrs, wherein the second reaction solvent is one selected from the group consisting of ethyl acetate, butyl acetate, methyl acetate, isopropyl acetate, methylene chloride and chloroform or any combination thereof; the acid is one of methanesulfonic acid, p-toluenesulfonic acid and p-toluenesulfonic acid monohydrate or any combination thereof;
(b1) after the reaction is completed, neutralizing an excessive acid with a base, adding a second poor solvent to precipitate a solid, filtering and then vacuum drying to obtain the compound of formula (10c), or a salt thereof.

In some embodiments, the base used to neutralize the excessive acid is one selected from the group consisting of potassium hydroxide, sodium carbonate, sodium bicarbonate, potassium carbonate, potassium bicarbonate, sodium phosphate, disodium hydrogen phosphate, potassium phosphate, and sodium hydroxide, or any combination thereof.

In some embodiments, the second poor solvent is one selected from the group consisting of n-heptane, n-hexane, cyclohexane, and methylcyclohexane, or any combination thereof.

In some embodiments, the base used to neutralize the excessive acid is potassium hydroxide; the second poor solvent is n-heptane.

In an embodiment of step (IV), the acid may be added to the second reaction solvent in batches.

The present application has beneficial effects as follows.
1) The present application provides a new compound of formula (9c), a compound of formula (10c), or salts thereof, and methods for preparing the same. After plenty of experiments for screening and verification, the inventor discovered unexpectedly that the compound of formula (9c), the compound of formula (10c) and salts thereof can be easily precipitated in the form of crystals, and are easier to be separated and purified, compared with the compound obtained in Preparation Examples 12b and 18 in the prior process (CN105705509A).
2) The present application provides a new method of preparing the compound of formula (1). Compared with the prior process, the new preparation method simplifies the production process, reduces the production cost, greatly improves the product quality (The purity of the crude product can be more than 99%), and is suitable for industrial production.
3) The present application provides use of the compound of formula (9c) and the compound of formula (10c) in the preparation of the compound of formula (1). Since the compound of the formula (9c) and the compound of the formula (10c) or salts thereof are easier to be purified, the drug quality can be controlled advantageously.

DESCRIPTION OF THE DRAWINGS

In order to illuminate the examples of the present application and the prior art more clearly, the figures used in the examples and the prior art are briefly described below. The figures described below are apparently part of the examples of the application. Other drawings may be obtained by those skilled in the art in view of these drawings without any creative effort.

DETAILED DESCRIPTION OF THE INVENTION

Reference is made to the following examples for a more complete understanding of the technical problem solved by the present application, technical solution and technical effect. In the following examples, unless otherwise specified, the experiments are generally performed under a condition that is conventional or recommended by the manufacturer; the raw material and reagent are commercially available or prepared according to a prior process. The percentages, ratios or parts are expressed by weight.

In a preferred embodiment of the present application, the complete reaction route for preparing the compound of formula (1) is:

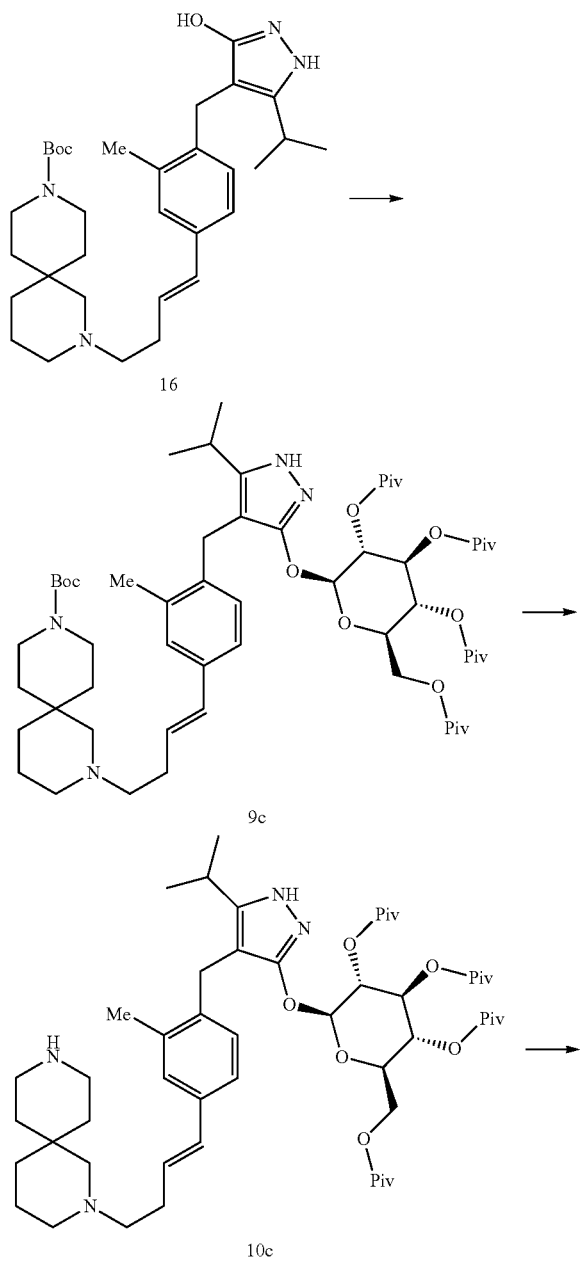

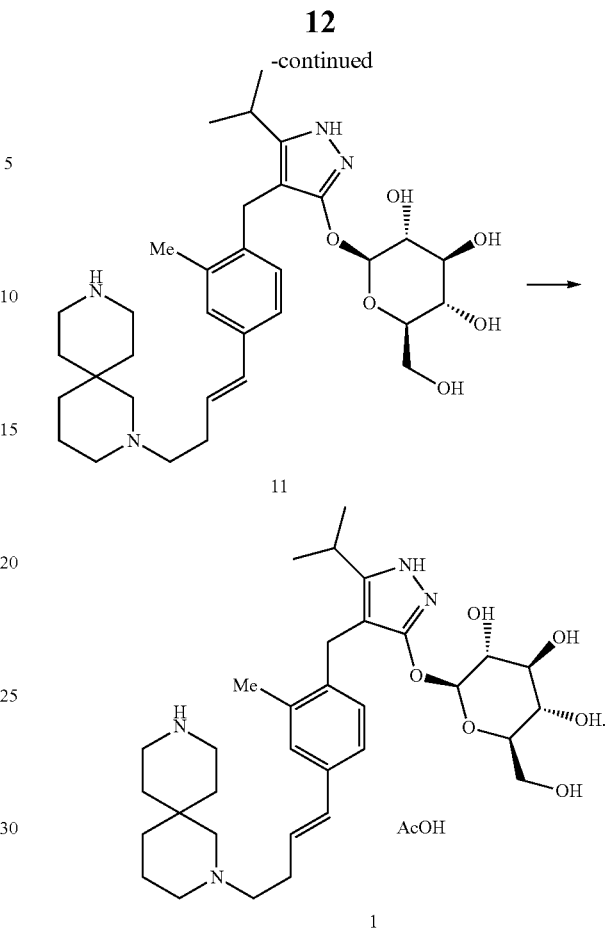

The above is only one of the reaction routes for the purpose of the present application, and does not limit the present application.

The compounds of formulae (16) and (17) can be prepared by a prior process, which is not described herein.

Example 1

Figure 1:
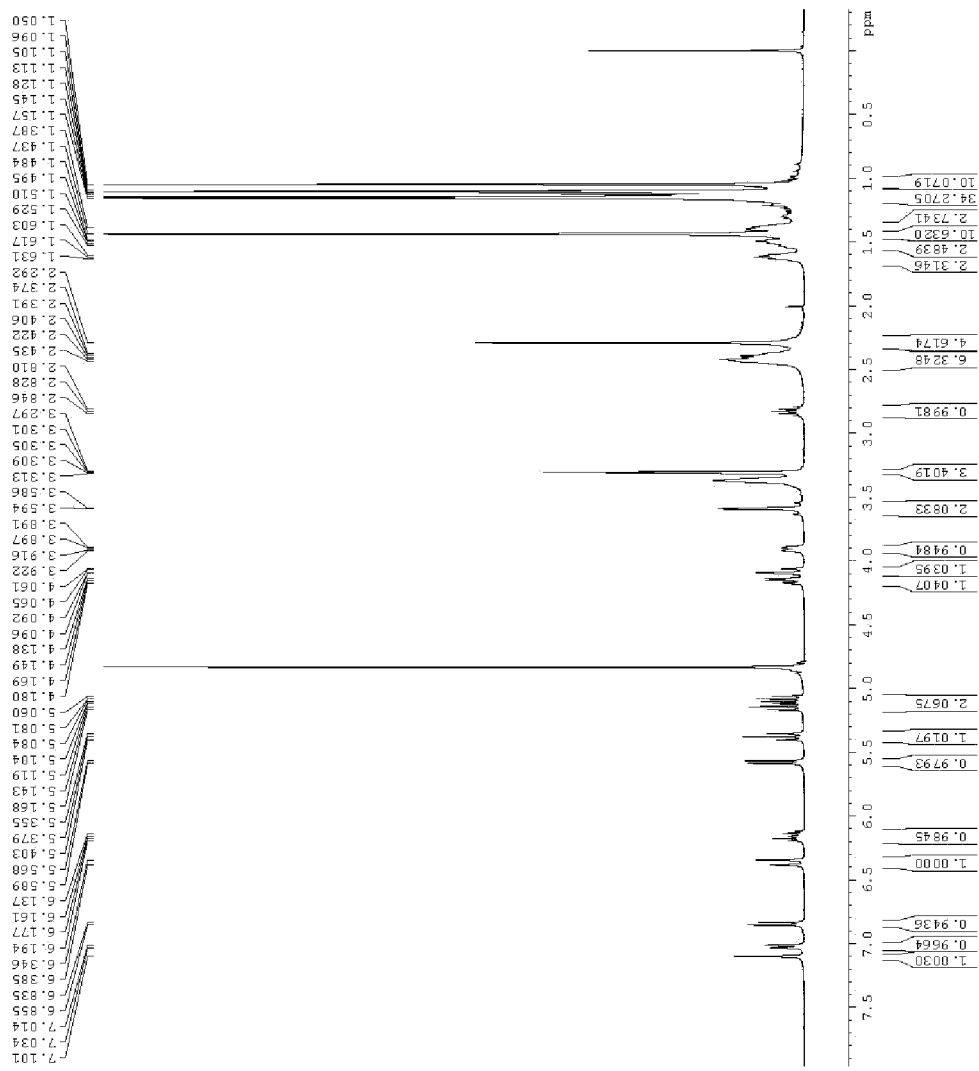
FIG. 1 shows an NMR spectrum of the compound of formula (9c)

626 g of the compound of formula (16), 6 L of acetonitrile, 840 g of cesium carbonate, and 1770 g of 2,3,4,6-tetra-O-pivaloyl-α-D-glucosyl bromide (the compound of formula (17)) was added to a reaction kettle in sequence, heated to 40-45° C., and reacted for 4-5 hrs. The reaction was then cooled to 20-25° C. and filtered, and the resulting solid was rinsed once with acetonitrile. The resulting filter cake was dissolved with 8 L ethyl acetate and 10 L water, and then the resultant was layered and separated. The organic phase was concentrated to about 3 L, and 10 L of acetonitrile was added thereto. The resultant was stirred for 12 hrs, and a solid was precipitated and filtered. The resulting filter cake was rinsed with acetonitrile, and vacuum-dried at 60° C. for 24 hrs to obtain 652 g of the compound of formula (9c) as an off-white crystal with a yield of 61%, a purity of 98.52% measured by HPLC, a melting point of 180.0-182.1° C. $^1$H NMR (400 MHz, MeOD) (see FIG. 1): δ7.10 (s, 1H), 7.03 (d, J=8.0 Hz, 1H), 6.86 (d, J=8.0 Hz, 1H), 6.39 (d, J=15.6, 1H), 6.19-6.12 (m, 1H), 5.59 (d, J=8.4 Hz, 1H), 5.40-5.35 (t, J=9.6 Hz, 1H), 5.17-5.06 (m, 2H), 4.18-4.14 (dd, J=12.4 Hz, 4.4 Hz, 1H), 4.10-4.06 (dd, J=12.4 Hz, 1.6 Hz, 1H), 3.92-3.89 (dd, J=10 Hz, 2.4 Hz, 1H), 3.64-3.54 (dd, J=20 Hz, 16.8 Hz, 2H), 3.31-3.30 (m, 4H), 2.86-2.79 (m, 1H), 2.37-2.29

(m, 11H), 1.63-1.38 (m, 17H), 1.15-1.05 (m, 42H). MS (m/z): 1035.7 (M+H), 1057.6 (M+Na).

Figure 2:
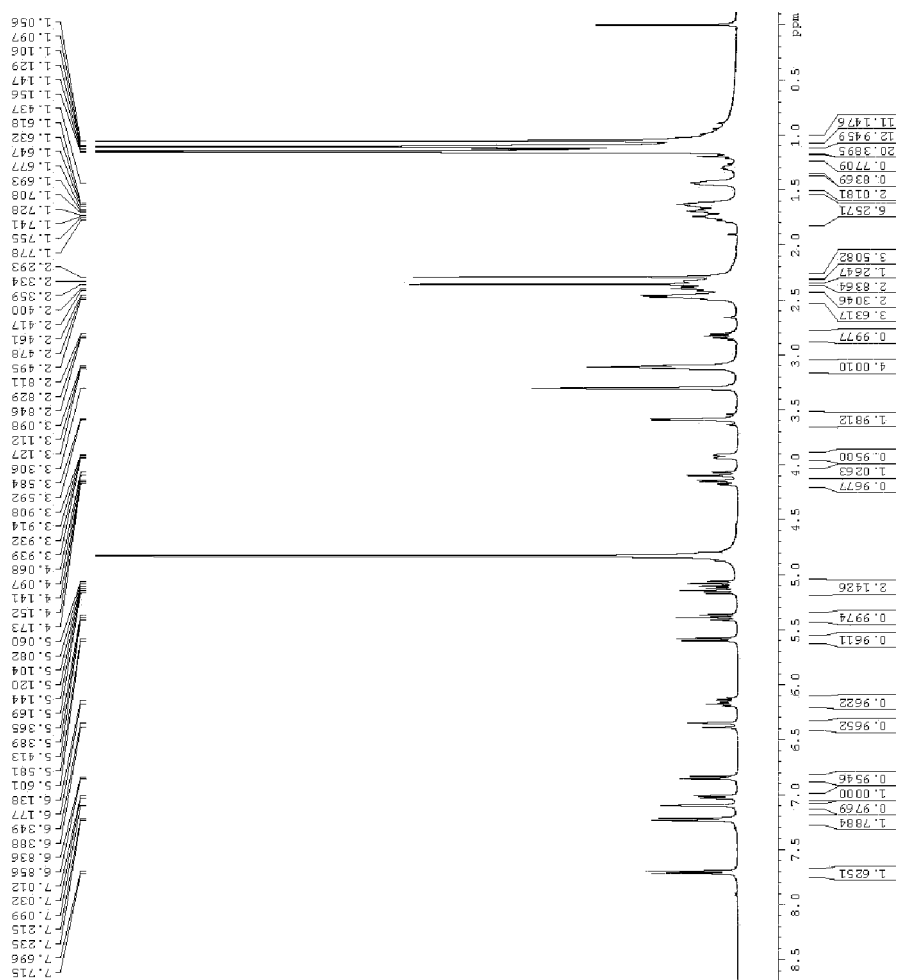
FIG. 2 shows an NMR spectrum of the compound of formula (10c)

640 g of the compound of formula (9c) and 6.4 L of ethyl acetate were added to a reaction kettle in sequence, and cooled to 15-20° C. 1176 g of p-toluenesulfonic acid monohydrate was added in batches to react for 2-3 hrs. After the reaction, 3.5 L of 9% aqueous solution of potassium hydroxide was added and stirred for 10 min. The resultant was layered and separated, and the aqueous phase was discarded. The organic phase was washed with 3.5 L 9% and 3.5 L 3% of aqueous solution of potassium hydroxide in sequence and concentrated to 2.5 L. 21 L of n-heptane was added to the residue, and then stirred for another 12 hrs. The mixture was filtered and the filter cake was rinsed with n-heptane and vacuum dried at 60° C. for 24 hrs to obtain a white crystal, 550 g of p-toluenesulfonate of the compound of formula (10c), with a yield of 80%, a purity of 97.59%, and a melting point of 168.0-169.2° C. $^1$H NMR (400 MHz, MeOD) (see FIG. 2): δ7.72 (d, J=7.6 Hz, 2H), 7.24 (d, J=8.0 Hz, 2H), 7.10 (s, 1H), 7.03 (d, J=8.0 Hz, 1H), 6.86 (d, J=8.0 Hz, 1H), 6.39 (d, J=15.6, 1H), 6.19-6.12 (m, 1H), 5.60 (d, J=8.0 Hz, 1H), 5.41-5.37 (t, J=9.6 Hz, 1H), 5.17-5.06 (m, 2H), 4.18-4.14 (dd, J=12.4 Hz, 4.0 Hz, 1H), 4.10-4.07 (d, J=11.6 Hz, 1H), 3.94-3.91 (dd, J=7.2 Hz, 2.8 Hz, 1H), 3.64-3.54 (dd, J=20.0 Hz, 16.8 Hz, 2H), 3.31-3.30 (m, 4H), 2.86-2.79 (m, 1H), 2.49-2.29 (m, 14H), 1.78-1.44 (m, 8H), 1.15-1.05 (m, 42H). MS (m/z): 935.7 (M+H).

Figure 3:
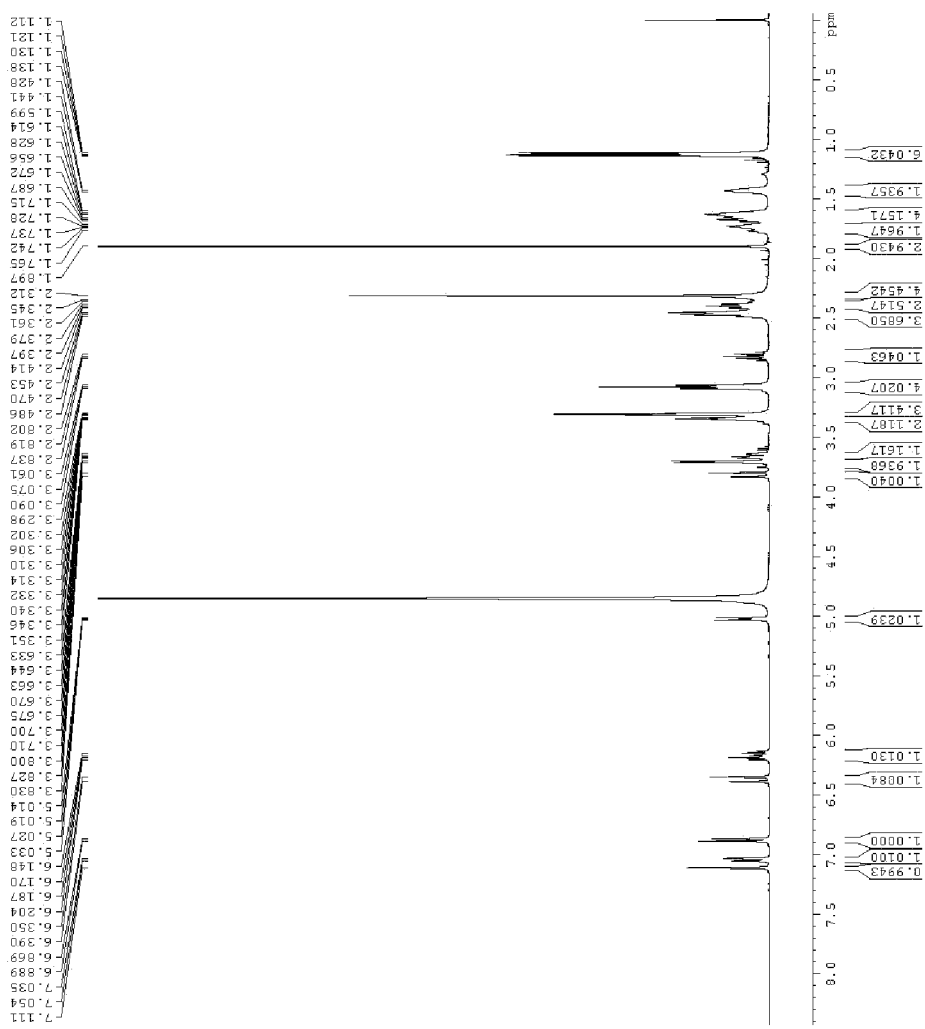
FIG. 3 shows an NMR spectrum of the compound of formula (1).

82.6 g of potassium hydroxide, 5.5 L of anhydrous ethanol and 550 g of p-toluenesulfonate of the compound of formula (10c) were added into a reaction kettle in sequence, and stirred at 45-50° C. for about 4 hrs. The reaction was cooled to 20-25° C. and filtered. The resulting solid was rinsed with ethanol. The filtrate and eluent was combined, added with 65 g of acetic acid, and stirred for 15 min. The reaction solution was concentrated to about 1.5 L under reduced pressure, then 52 g of acetic acid was added and stirred for 20 min 4.5 L of ethyl acetate containing 3% water and 160 mL of purified water were added dropwise, stirred for another 3-4 hrs and filtered. The filter cake was then rinsed with ethyl acetate containing 3% water. The solid was transferred to a reaction kettle. 500 mL of water was added, stirred for 18 hrs and filtered. The filter cake was rinsed successively with water and a mixed solvent of ethanol/ethyl acetate. The filter cake was vacuum dried at 35-40° C. for 4 hrs to obtain a white solid, 245 g of the compound of formula (1), with a yield of 75%, and a purity of 99.55%. $^1$H NMR (400 MHz, MeOD) (see FIG. 3): δ7.11 (s, 1H), 7.05 (d, J=7.6 Hz, 1H), 6.89 (d, J=8.0 Hz, 1H), 6.39 (d, J=16.0, 1H), 6.20-6.13 (dt, J=15.6 Hz, 6.8 Hz, 1H), 5.03-5.01 (m, 1H), 3.83 (d, J=11.2, 1H), 3.71-3.59 (m, 3H), 3.35-3.30 (m, 4H), 3.09-3.06 (t, J=6 Hz, 4H), 2.87-2.77 (m, 1H), 2.49-2.31 (m, 6H), 2.30 (s, 3H), 2.26 (s, 2H), 1.90 (s, 3H), 1.78 (m, 2H), 1.68 (m, 2H), 1.65 (m, 2H), 1.44-1.43 (m, 2H), 1.13 (d, J=6.8 Hz, 3H), 1.11 (d, J=6.8 Hz, 3H), MS (m/z): 599.5 (M+H).

Example 2

5.00 kg of maleate of the compound of formula (16), 40 L of tetrahydrofuran, 5.47 kg of potassium phosphate, and 11.67 kg of 2,3,4,6-tetra-O-pivaloyl-α-D-glucosyl bromide (the compound of formula (17)) were added to a reaction kettle in sequence, heated to 40-45° C., and reacted for 4-5 hrs. Then, the reaction was cooled to 15-25° C. and filtered. The resulting solid was rinsed once with tetrahydrofuran. The filter cake was dissolved with 36 L of ethyl acetate and 20 L of water and the resultant was layered and separated. The organic phase was concentrated to about 18 L. 64 L of acetonitrile was added, stirred for 15 hrs and filtered. The filter cake was rinsed with acetonitrile and vacuum dried at 60° C. for 24 hrs to obtain an off-white crystal, 4.50 kg of the compound of formula (9c), with a yield of 57%, and a purity of 99.19% measured by HPLC.

4.45 kg of the compound of formula (9c) and 45 L of butyl acetate were added to a reaction kettle in sequence, and cooled to 15-20° C. 4.13 kg of methanesulfonic acid was added in batches, and the reaction was performed for 2-3 hrs. 22 L of 9% aqueous solution of potassium hydroxide was added to the reaction, and stirred for 10 min. The resultant was layered and separated, and the aqueous phase was discarded. The organic phase was washed with 10 L 9%, 4.5 L 10% and 2 L 2.5% of aqueous solution of potassium hydroxide in sequence and concentrated to 15 L. 68 L n-heptane was added to the residue, then stirred for another 12 h, and filtered. The filter cake was rinsed once with n-heptane. The solid was vacuum dried at 60° C. for 24 hrs to obtain a white crystal, 4.37 kg of the methanesulfonate of the compound of formula (10c), with a yield of 99% and a purity of 97.94%.

0.73 kg of potassium hydroxide, 43 L of methanol and 4.30 kg of the compound of formula (10c) were sequentially added into a reaction kettle, and stirred at 45-50° C. for 4 hrs. The reaction was cooled to 20-25° C., and filtered. 0.56 kg of acetic acid was added to the filtrate and stirred for 15 min. The reaction solution was concentrated to about 15 L under reduced pressure, 0.40 g of acetic acid was added, and stirred for 10 min 39 L of ethyl acetate containing 3% water and 1.3 L of purified water were added dropwise, then stirred for about 2 hrs and filtered.

The filter cake was rinsed once with ethyl acetate containing 3% water. The solid was transferred to a reaction kettle, added with 3.5 L of water, stirred for 18 hrs and filtered. The filter cake was washed successively with water and a mixed solvent of ethanol/ethyl acetate. The filter cake was vacuum dried at 35-40° C. to obtain a white solid, 1.84 kg of the compound (1) of formula (1), with a yield of 67%, and a purity of 99.65%.

In summary, this application greatly simplifies the preparation process through the new key intermediate compound of formula (9c), and the compound of formula (10c) or the salt thereof. At the same time, since the key intermediates, the compound of formula (9c) and the compound of formula (10c) or the salt thereof, can be precipitated in the form of crystals, it is easy to be purified, which improves the purity of compound of formula (1) (the purity of the crude product can be more than 99%) compared with the original synthetic route, so that the quality of the product can be effectively controlled. At the same time, the preparation method of the present application also shortens the production cycle, reduces the production cost, effectively improves the production efficiency, and is more conducive to industrial production.

The examples above intend to illustrate the essence of the present application, rather than to limit the scope thereof. Those skilled in the art should understand that the present application can be modified or equivalently replaced without departing from the essence and scope of the present application.

The invention claimed is:

1. A compound of formula (9c):

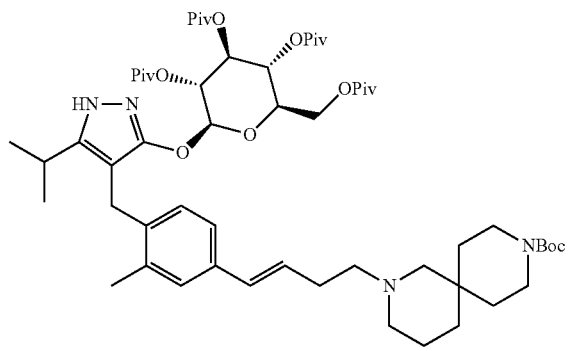

wherein Piv is pivaloyl.

2. A method for preparing the compound of formula (9c) according to claim 1, comprising reacting a compound of formula (16) or a salt thereof with a compound of formula (17) to obtain the compound of formula (9c):

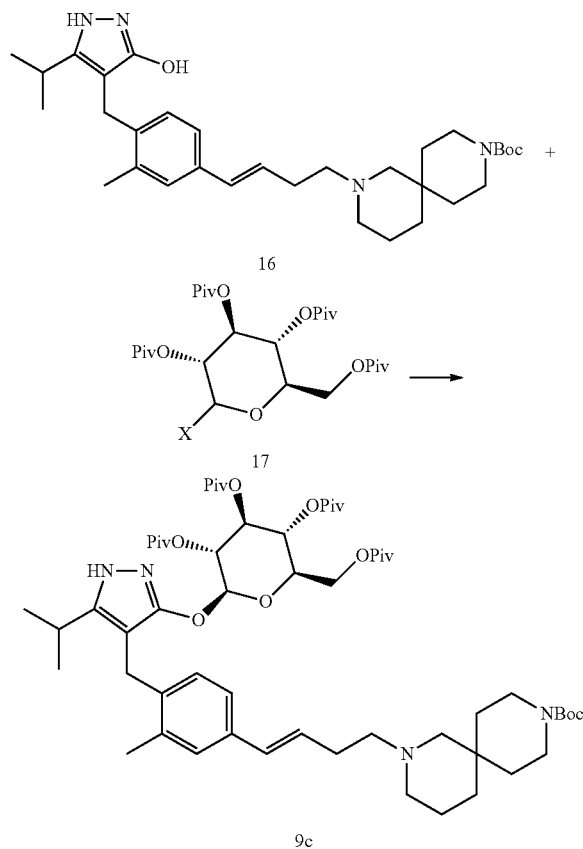

wherein, Piv is pivaloyl and X is a leaving group.

3. The method according to claim 2, wherein the leaving group X is selected from the group consisting of halogen, methanesulfonate, triflate or p-toluenesulfonate.

4. The method according to claim 2, wherein a salt of the compound of formula (16) is selected from the group consisting of hydrochloride, acetate, maleate or succinate.

5. The method according to claim 2, wherein the reaction is performed in a first reaction solvent under a basic condition.

6. The method according to claim 2 comprising:
(1) reacting the compound of formula (16) or a salt thereof with the compound of formula (17) in a first reaction solvent under a basic condition for 4-5 hrs at a temperature of 40-45° C.;
(2) after the reaction is completed, cooling, filtering, dissolving a filtered solid into a first organic solvent and water to remove an inorganic salt, adding a first poor solvent to precipitate a solid, filtering and then vacuum drying to obtain the compound of formula (9c).

7. The method according to claim 5, wherein a base used in the basic condition is one selected from the group consisting of carbonate, phosphate, bicarbonate and hydrogen phosphate, or any combination thereof; and the first reaction solvent is one selected from the group consisting of acetonitrile, N,N-dimethylformamide, tetrahydrofuran and ethyl acetate, or any combination thereof.

8. An intermediate compound of formula (10c) or a salt thereof,

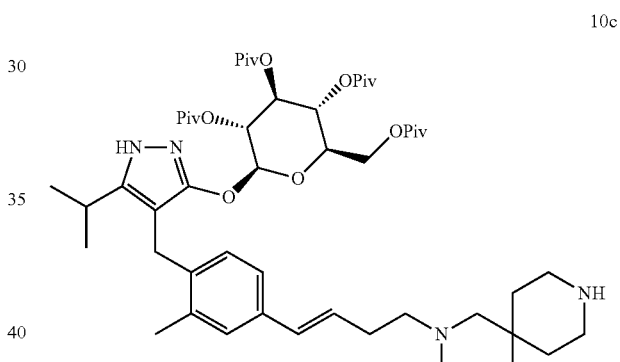

wherein Piv is pivaloyl.

9. A method for preparing the intermediate compound of formula (10c) or a salt thereof according to claim 8, comprising reacting a compound of formula (9c) with an acid to obtain the compound of formula (10c) or a salt thereof;

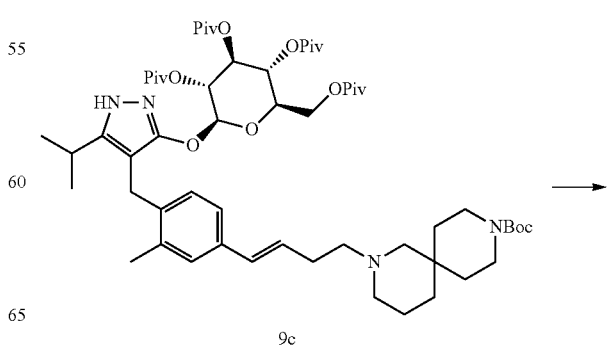

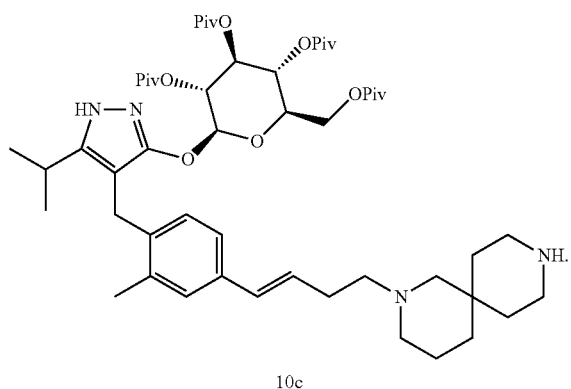

10c

10. The method for preparing the intermediate compound of formula (10c) or a salt thereof according to claim 9, comprising:

(a) reacting the compound of formula (9c) with the acid in a second reaction solvent for 2-3 hrs at a temperature of 15-20° C., wherein the second reaction solvent is one selected from the group consisting of ethyl acetate, butyl acetate, methyl acetate, isopropyl acetate, methylene chloride and chloroform, or any combination thereof; and the acid is one of methanesulfonic acid, p-toluenesulfonic acid and p-toluenesulfonic acid monohydrate, or any combination thereof;

(b) after the reaction is completed, neutralizing an excessive acid with a base, adding a second poor solvent to precipitate a solid, filtering and then vacuum drying to obtain the compound of formula (10c) or a salt thereof.

11. A method for preparing a compound of formula (1), comprising:

(I) subjecting a compound of formula (10c) or a salt thereof to hydrolysis or alcoholysis under a basic condition to obtain a compound of formula (11);

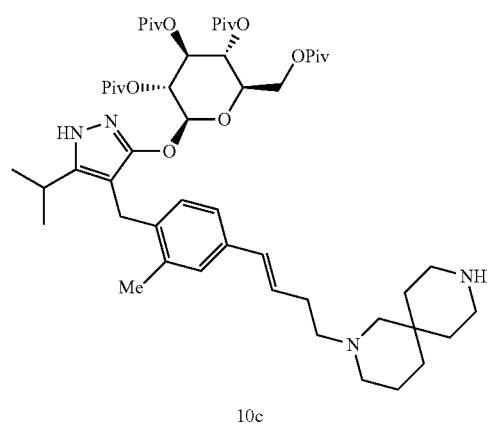

10c

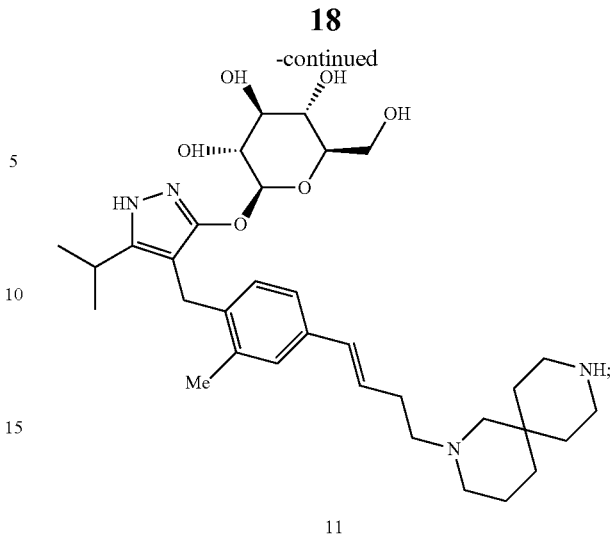

11

(II) reacting the compound of formula (11) with acetic acid to obtain the compound of formula (1):

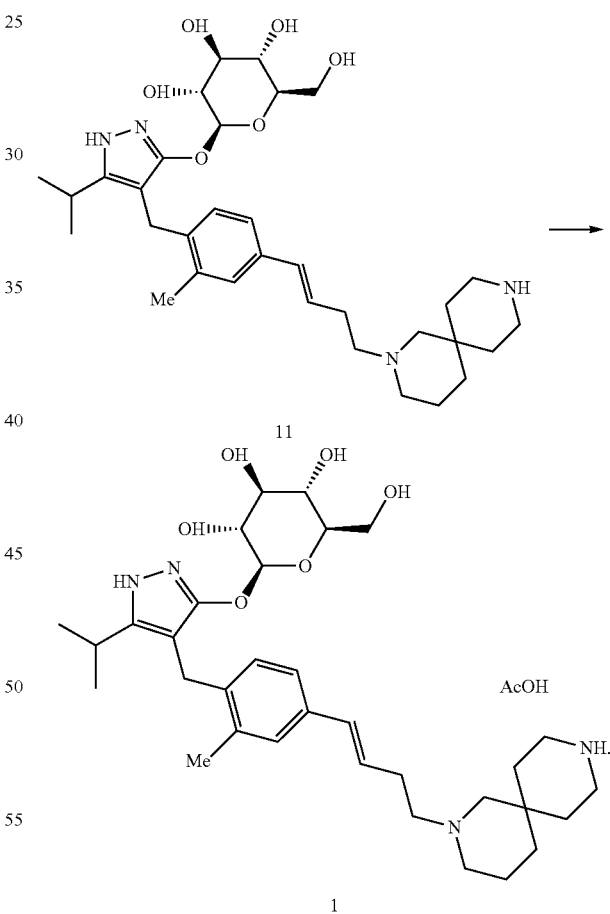

12. The method for preparing the compound of formula (1) according to claim 11, wherein the compound of formula (10c) or a salt thereof is obtained by:

(III) reacting a compound of formula (16) or a salt thereof with a compound of formula (17) to obtain a compound of formula (9c), wherein X is a leaving group and Piv is pivaloyl;

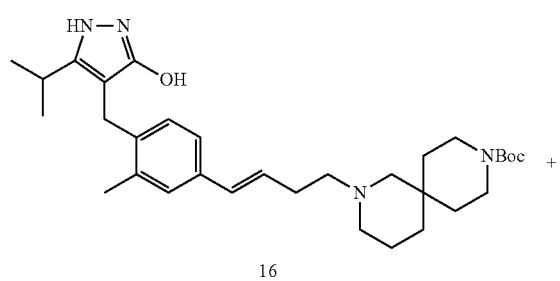

16

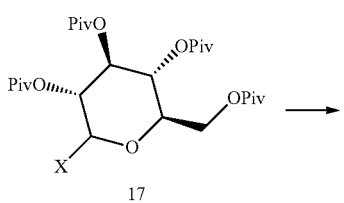

17

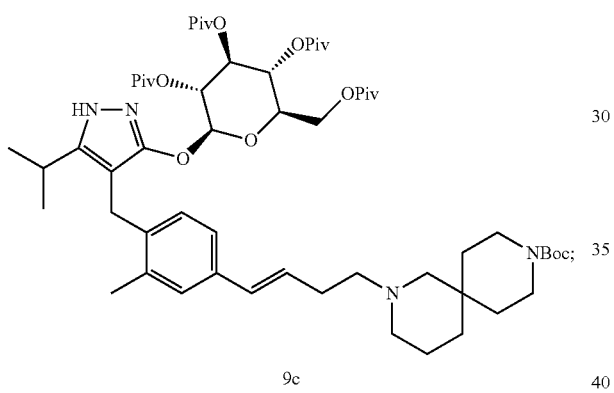

9c and (IV) reacting the compound of formula (9c) with an acid to obtain the compound of formula (10c) or a salt thereof;

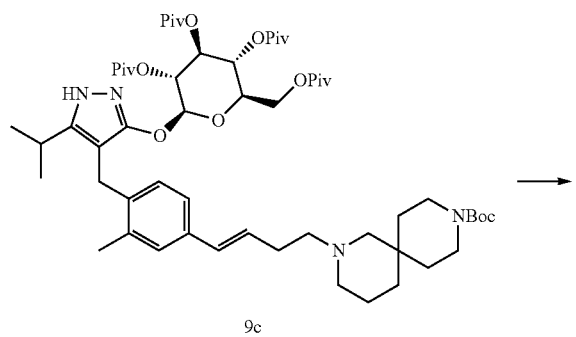

9c

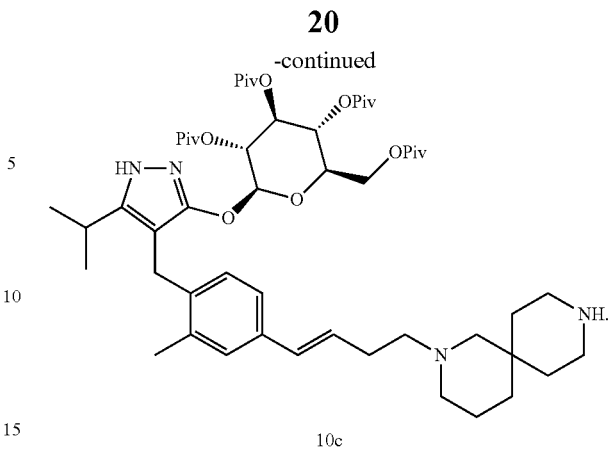

10c

13. The method according to claim 11, wherein
step (I) is performed by:
subjecting the compound of formula (10c) or a salt thereof to hydrolysis or alcoholysis under a basic condition at a temperature of 45-50° C., and cooling and filtering after the reaction is completed to obtain a filtrate containing the compound of formula (11); wherein the hydrolysis is performed with one or both of water-containing ethanol and methanol; the alcoholysis is performed with one or both of anhydrous ethanol and methanol; a base used in the basic condition is one selected from the group consisting of potassium hydroxide, sodium hydroxide, DBU, sodium methoxide and sodium ethoxide, or any combination thereof; and
step (II) is performed by:
adding acetic acid into the obtained filtrate containing the compound of formula (11) and stirring, then adding ethyl acetate and water dropwise, stirring for another 3-4 hrs; and after the reaction is completed, filtering, rinsing, and vacuum drying to obtain the compound of formula (1).

14. The method according to claim 12, wherein
step (III) is performed by:
reacting the compound of formula (16) or a salt thereof with the compound of formula (17) under a basic condition in a first reaction solvent at a temperature of 40-45° C. for 4-5 hrs to obtain the compound of formula (9c), wherein the leaving group X of the compound (17) is selected from the group consisting of halogen, methanesulfonate, triflate and p-toluenesulfonate; a salt of the compound of formula (16) is selected from the group consisting of hydrochloride, acetate, maleate and succinate; the base used in the basic condition is one selected from the group consisting of carbonate, phosphate, bicarbonate and hydrogen phosphate, or any combination thereof; the first reaction solvent is one selected from the group consisting of acetonitrile, N,N-dimethylformamide, tetrahydrofuran and ethyl acetate, or any combination thereof; after the reaction is completed, cooling, filtering, dissolving a filtered solid into a first organic solvent and water to remove an inorganic salt, adding a first poor solvent to precipitate a solid, and filtering and then vacuum drying to obtain the compound of formula (9c; and
step (IV) comprises:
(a1) reacting the compound of formula (9c) with an acid in a second reaction solvent at a temperature of 15-20° C. for 2-3 hrs, wherein the second reaction solvent is one selected from the group consisting of ethyl acetate, butyl acetate, methyl acetate, isopropyl acetate, methylene chloride and chloroform, or any combination thereof; and the acid is one of methanesulfonic acid, p-toluenesulfonic acid and p-toluenesulfonic acid monohydrate, or any combination thereof; and (b1) after the reaction is completed, neutralizing an excessive acid with a base, adding a second poor solvent to precipitate a solid, filtering and then vacuum drying to obtain the compound of formula (10c) or a salt thereof.

15. The method according to claim 6, wherein the first organic solvent is ethyl acetate.

16. The method according to claim 6, wherein the first poor solvent is one selected from the group consisting of acetonitrile, methyl tert-butyl ether, diethyl ether, n-heptane, n-hexane, and cyclohexane, or any combination thereof.

17. The intermediate compound of formula (10c) or a salt thereof according to claim 8, wherein a salt of the compound of formula (10c) is methanesulfonate or p-toluenesulfonate.

18. The method for preparing the intermediate compound of formula (10c) or a salt thereof according to claim 10, wherein the acid is added into the second reaction solvent in batches in step (a); and the base used to neutralize the excessive acid is one selected from the group consisting of potassium hydroxide, sodium carbonate, sodium bicarbonate, potassium carbonate, potassium bicarbonate, sodium phosphate, disodium hydrogen phosphate, potassium phosphate, and sodium hydroxide, or any combination thereof; and the second poor solvent is one selected from the group consisting of n-heptane, n-hexane, cyclohexane, and methylcyclohexane, or any combination thereof in step (b).

* * * * *